United States Patent [19]

Rand

[11] Patent Number: 4,983,159

[45] Date of Patent: Jan. 8, 1991

[54] INDUCTIVE HEATING PROCESS FOR USE IN CAUSING NECROSIS OF NEOPLASMS AT SELECTIVE FREQUENCIES

[76] Inventor: Robert W. Rand, 521 N. Bristol St., Los Angeles, Calif. 90049

[21] Appl. No.: 908,190

[22] Filed: Sep. 17, 1986

Related U.S. Application Data

[63] Continuation-in-part of Ser. No. 715,254, Mar. 25, 1985, abandoned.

[51] Int. Cl.⁵ ............................................. A61N 2/00
[52] U.S. Cl. ....................................... 600/9; 600/12; 128/804; 219/10.57
[58] Field of Search .................... 128/1.3–1.5, 128/804, 399; 219/10.57; 600/9–13

[56] References Cited

U.S. PATENT DOCUMENTS

| | | | |
|---|---|---|---|
| 3,474,777 | 10/1969 | Figge | 128/1.3 |
| 4,106,488 | 8/1978 | Gordon | 128/399 |
| 4,269,826 | 5/1981 | Zimmermann et al. | 128/1.3 |
| 4,323,056 | 4/1982 | Borrelli et al. | 128/1.3 |
| 4,359,453 | 0/1982 | Gordon | 424/1 |
| 4,369,345 | 1/1983 | Czerlinski | 128/1.5 |
| 4,392,040 | 7/1983 | Rand et al. | 128/1.5 |

FOREIGN PATENT DOCUMENTS

| | | | |
|---|---|---|---|
| 1284528 | 12/1968 | Fed. Rep. of Germany | 128/1.5 |
| 2508802 | 1/1983 | France | 128/1.3 |

OTHER PUBLICATIONS

Tatsuya Kobayashi et al., Magnetic Induction Hyperthermia for Brain Tumor Using Ferromagnetic Implant with Low Curie Temperature, J. Neuro-Oncology, 4, 175–181 (1986).

*Primary Examiner*—Ruth S. Smith
*Attorney, Agent, or Firm*—Herb Boswell

[57] ABSTRACT

A process of effecting necrosis of neoplasms in warm blooded animals as a result of hyperthermia of the neoplasm includes injecting particles into the warm blooded animals in proximity of the neoplasm. The particles are capable of exhibiting hysteresis heating when subjected to an alternating magnetic field. Further, the particles are of a size of at least two microns, or greater, so as to be incapable of being intracellularly absorbed within the cells of either the viable tissue of the animal or the neoplastic tissue. After interjecting the particles in association with the neoplasm, the area of the neoplasm is then subjected to an alternating magnetic field. This field is of a frequency greater than that sufficient to cause any appreciable neuromuscular response to the alternating magnetic field, and is less than that capable of causing any detrimental eddy current heating and/or dielectric heating of viable healthy tissue of the warm blooded animal. The neoplasm is maintained within the field for a time sufficient to heat the particles and the neoplasm, with which the particles are associated, to a temperature of at least 42° C. to cause necrosing of the neoplasm.

8 Claims, No Drawings

INDUCTIVE HEATING PROCESS FOR USE IN CAUSING NECROSIS OF NEOPLASMS AT SELECTIVE FREQUENCIES

CROSS REFERENCE TO RELATED APPLICATIONS

This application is a continuation in part of my prior application Ser. No. 715,254, filed Mar. 25, 1985 now abandoned and entitled Inductive Heating Process For Use In Causing Necrosis of Neoplasms At Selective Frequencies, the entire contents of which are herein incorporated by reference.

BACKGROUND OF THE INVENTION

This invention is directed to a process of necrosing neoplasms as a result of hyperthermia of the neoplasm induced by hysteresis heating at selected frequencies of particles associated with the neoplasm.

It is a recognized medical fact that certain surgical invasions of neoplastic tumors in warm blooded animals can lead to adverse consequences. It is recognized that during the surgical removal of such neoplastic tumors, certain cells may be dislodged and entered into the general circulation of the war blooded animal to be carried to a distal site wherein an implantation of these cells occurs in the host. Growth of the neoplastic cells at the secondary site follows perpetuating the disease.

It is has further been recognized that if a neoplastic tumor could be destroyed without surgical intervention of the tumor site, the above described secondary spread of the neoplastic tumor would not occur. It is difficult enough to manage the metastasis of the tumor without further introducing secondary spread of the tumor by invasive surgical techniques.

Of the approaches taken to treat the tumor without surgical intervention of the same, the most common are radiation therapy and chemotherapy. While shortwave radiation such as X-rays and gamma rays are capable of destroying neoplastic tumors, they must, in fact, travel through overlaying body organs in order to reach the tumor site, and, if this form of radiation is not totally attenuated by the tumor, they will pass through further body organs beyond the tumor. The effect of the X-ray and gamma ray radiation on the normal body organs leads to serious side effects for this form of therapy.

Chemotherapy is also not without its side effects. The chemotherapeutic agent generally is distributed throughout the body of the warm blooded animal irrespective of its route of administration. It has been the goal of chemotherapy to develop chemotherapeutic agents which are only tumor specific acting agents and not agents which express their chemical effects on the general cellular population of the warm blooded animal. While strides have been made to develop agents which express their chemical effect on the more rapid growing tumor cells, other rapid growing body cells are also affected. This too leads to side effects in the use of these therapeutic agents.

It was suggested several decades ago to utilize hyperthermia to selectively destroy neoplastic tumors without concurrently destroying healthy tissue. Early attempts in this area involve surgical intervention into the tumor area of the warm blooded animal followed by hyperthermia treatment of the tumor site upon exposure of the same. Insofar as this technique involves surgical intervention into the body, aside from the necessity of a surgical procedure, it also potentially exposes the patient to dislodging of tumor cells and implantation of the same at secondary sites as discussed above. In order to circumvent surgical intervention into the body, induction heating hyperthermia has been explored.

In my prior U.S. Pat. No. 4,392,040, myself and my co-inventors thereof discuss certain hyperthermia procedures. Additionally, others, such as Borrelli et al, as is discussed in their U.S. Pat. No. 4,323,056, have explored this for control of neoplastic tumors. As is discussed in both of these two patents, both radio frequency and microwave frequency treatment have been explored.

Microwave radiation is utilized in diathermy. Unfortunately, the tissue of warm blooded animals is rather opaque to microwaves and the heating which results from exposure to microwaves occurs essentially at the body surface. Because of the attenuation of the microwaves by the body mass, little or no heating can be affected at deep seated points within the body cavity without excessive heating of the body surface. Because of this, hyperthermia treatment of imbedded neoplastic tumors is not possible without necrosing surface layers of the body.

In order to circumvent the above problems with prior known technologies, both myself and my co-inventors in my U.S. Pat. No. 4,392,040, Borrelli et al in the above referred to U.S. Pat. No. 4,323,056, and Gordon in U.S. Pat. No. 4,106,488 and U.S. Pat. No. 4,303,636 have suggested the use of hysteresis heating for deep seated neoplastic tumors. By exposing certain materials to magnetic fields, these materials can be heated. This heating ca be effected utilizing several mechanisms. First of these is hysteresis heating which results when these materials are positioned within an alternating magnetic field and results because of the hysteresis loss due to the varying magnetic flux on reversal of the field. The hysteresis heating is independent of particle size and, depending on the particular material, within a certain frequency range it is proportional to the frequency of the magnetic field.

A second type of heating is eddy current heating which results from current loops which are created in response to an alternating magnetic field. Eddy current heating is proportional to the electrical resistance of the conductor and is dependent upon particle size. It is further proportional to the frequency squared of the alternating magnetic field. It is known that eddy current heating can be reduced by reducing the particle size and, in fact, this technique is practiced in the electrical arts to reduce eddy current effects.

A further effect is encountered in treating biological specimens with alternating magnetic fields. This effect is dielectric heating which occurs in materials which are poor conductors. Dielectric heating results from reverse of polarization in the conductors in response to reversal of a high frequency electrical field.

As Borrelli stated in U.S. Pat. No. 4,323,056, the early implantation of powdered magnetic materials while demonstrative of the usefulness of localized induction heating to destroy neoplasms, was mitigated because of the heating of normal tissue and necrosis of the same due to dielectric heating resulting from the ionic conductivity of body tissue and fluids.

Because of the accompanying dielectric and/or eddy current heating of healthy tissue which accompanies hysteresis heating at higher frequencies, both myself and my co-inventors and Borrelli et al in U.S. Pat. Nos.

4,392,040 and 4,323,056, suggested the use of frequencies at, or below, 10 KHz, This serves to effectively eliminate destruction of healthy tissue resulting from concurrent dielectric and/or eddy current heating during hysteresis heating of metallic particles within a body.

I have found, however, that treatment of neoplastic tumors, utilizing hysteresis heating of particles within a body, at frequencies below 10 KHz, is also not without its qualifications. I have found, when warm blooded animals are placed within a coil as is described in my prior U.S. Pat. No. 4,392,040, and exposed to an alternating magnetic field in the frequency range described in that patent, and, further, as is included within the frequency range of the Borrelli et al U.S. Pat. No. 4,323,056, that the alternating magnetic field induces certain neuromuscular responses in the warm blooded animal, resulting in muscular movement and increase of muscular tone. This occurs because of the induction of minute amounts of current flow within the nerves controlling these muscles. Current flow in the nerves leads to muscle tonic and clonic contractions. This is extremely painful and, further, this condition can lead to intramuscular bleeding with the breakdown of the myosin in the muscle. The myosin can then be transported to the kidney wherein it clogs the kidney leading to kidney failure and death.

In order to circumvent the neuromuscular response, it is necessary to concurrently administer a muscular blocking agent such as curare. Curare is a general muscle relaxant and, as such, also expresses its effect on the lungs. Because of this it is necessary to anesthetize the patient under a general anesthesia and place the patient on a respirator in order to affect breathing until such time as the muscle relaxant state is removed.

BRIEF DESCRIPTION OF THE INVENTION

In view of the above, it is the broad object of this invention to provide for a new and improved process of affecting necrosis of neoplasms in warm blooded animals. It is a further object of this invention to effect this necrosis by associating particles capable of exhibiting hysteresis heating with the neoplasm and causing said hysteresis heating of said particles. It is an additional object of this invention to effect such hysteresis heating of said particles by exposing said particles to an alternating magnetic field of a frequency which is above that which causes neuromuscular responses in warm blooded animals and which is below that wherein the tissue of the warm blooded animal exhibits either substantial eddy current and/or dielectric heating in response to the alternating magnetic field.

These and other objects, as will be evident from the remainder of this specification, are achieved in a process of effecting necrosis of neoplasms in warm blooded animals as a result of hyperthermia of the neoplasm which comprises: introducing particles into said warm blooded animal in the proximity of said neoplasm so as to associate said particle with said neoplasm, said particles capable of exhibiting hysteresis heating, said particles of a size of at least two microns in diameter so as to be incapable of being intracellularly absorbed, said particles further having a curie point in the range of 42° C. to 90° C.; subjecting the area of said warm blooded animal wherein said neoplasm having said particles associated therewith is located to an alternating magnetic field, said field of a frequency greater than 25 KHz and less than 50 KHz wherein said field is capable of causing hysteresis heating of said particles but is insufficient to substantially cause eddy current and dielectric heating of the surrounding tissue of said warm blooded animal and further said field is of a frequency greater than that capable of causing a neuromuscular response to said field in said warm blooded animal; maintaining said neoplasm within said field for a time sufficient to heat said particles and said neoplasm with which said particles are associated to a temperature of at least 42° C.

The particle size is chosen such that the particles are of a sufficient density so as to achieve efficient hysteresis heating in a localized area to effect the necrosis of the neoplasm. To achieve this the particle size is chosen so as to be a minimum of at least two microns in diameter. The frequency of the alternating magnetic field is chosen to be at least 25 KHz to avoid neuromuscular response and to be less than 50 KHz to avoid any significant eddy current heating or dielectric heating of body tissue.

This invention utilizes certain principles and/or concepts as are set forth in the claims appended hereto. Those skilled in the medical arts will realize that these principles and concepts may be utilized in a variety of different ways without departing from the scope of the invention as set forth in the claims appended hereto.

DETAILED DESCRIPTION OF THE INVENTION

In my prior U.S. Pat. No. 4,392,040, the entire contents of which are herein incorporated by reference, I and my co-inventors describe a process and an apparatus for performing this process The process is for causing necrosis of neoplasms as a result of hyperthermia of the neoplasms resulting from injection of magnetic particles into the tissue in proximity with the neoplasm and subjecting these particles to an alternating magnetic field to cause hysteresis heating of the particles. As noted above, the particles are exposed to an alternating magnetic field below 5 KHz preferably at 2 KHz. At these particular frequencies there is little or no concurrent respective eddy current or dielectric heating of this tissue be it surrounding tissue or neoplastic tissue. This allows for the necrosis of the neoplasm as a result of the hysteresis heating without any concurrent damage to healthy tissue. Unfortunately, as noted above, the use of frequencies in this range is accompanied by a neuromuscular response which requires corrective measures of a nature requiring supportive medical personnel and apparatus. Irrespective of the supporting personnel and apparatus, anytime a general anesthetic is utilized a certain degree of inherent risk is introduced into the medical procedure.

The above referred to neuromuscular response is prevalent throughout the range of frequencies described in my U.S. Pat. No. 4,392,040, as well as those described in Borrelli et al U.S. Pat. No. 4,323,056. In a patient suffering from a neoplastic tumor wherein the prognosis is very poor, the potential side effects of a general anesthesia and of curare are of a lesser nature than the ultimate consequences of progression of the neoplastic disease state. In view of this, irrespective of any potential problems resulting from the general anesthetic or the curare, in these instances practice of the process of the above two referred to patents is indicated.

If, however, an alternating magnetic field of at least 25 KHz is utilized, the neuromuscular response to that alternating magnetic field is dramatically decreased, and, at about 30 KHz is absent. As such, utilization of an alternating magnetic field of at least 25 KHz, and preferably 30 KHz, eliminates the necessity of supportive general anesthesia and muscle relaxant therapy which is necessary at the lower frequencies indicated in U.S. Pat. Nos. 4,392,040 and 4,323,056.

Hysteresis heating of susceptible particles is achieved by positioning these particles within an alternating magnetic field. The hysteresis heating occurs upon each reversal of the magnetic field. Hysteresis heating is directly proportioned to the frequency of the field. It is further dependent upon the shape of the magnetic curve of the particle. Eddy current heating occurs in electrically conductive material and is due to current loops induced into the material when the material is positioned within a changing field. This heating is proportional to the electrical resistance of the conductor and is dependent on particle size. It is further proportional to the square of the frequency as opposed to simply the frequency for hysteresis heating. Dielectric heating occurs in materials which are poor conductors and results because of induced polarization within these conductors' in response to alternating electrical fields.

Dielectric heating in the body of the warm blooded animal results because of the ions within the fluids of the warm blooded animal. The effect of dielectric heating is utilized in a positive way in diathermy utilizing microwave range frequencies. The practice of this type of heating, however, is limited by certain restrictions based on approved frequencies approved by both the FDA and the FCC. One such approved frequency is 13.57 MHz.

Certain magnetic particles are susceptible to both hysteresis and eddy current heating. As the particle size is reduced, the eddy current heating effect is concurrently reduced. This, in effect, is utilized to advantage in the electrical arts to eliminate any current loss in certain electrical components by utilizing powdered magnetic material in these components.

When inserting particles in to a warm blooded animal, of necessity the particles must be of limited size. Therefore, eddy current heating of these particles, at least at lower frequencies, is proportionately much smaller than the hysteresis heating of the particles. The reduction of particle size results in reduction of eddy current heating of magnetic particles; but within the body tissues of a warm blooded animal, an alternating magnetic field reacting with the water molecules within the body of the warm blooded animal produces eddy current heating which increases upon increase of frequency in proportion to the frequency square. Thus, the eddy current heating of the tissue of the animal rises by a factor of the frequency squared as frequencies increased, but the eddy current heating of the particles, because of their small size, is of lesser consequence.

It is evident that while increasing the frequency of an alternating magnetic field may improve hysteresis heating of imbedded particles within the body of a warm blooded animal, this is accompanied by increased eddy current heating of the body tissues of the warm blooded animal in a mathematical relation, which leads to a greater increase of eddy current heating of the body compared to the hysteresis heating of the particles.

In saline it can be shown that dielectric heating is detectable at 500 KHz and becomes significant at about 1 MHz. Eddy current is minimally detectable at 0.4 KHz but has become significant at 100 KHz.

Gordon in the above two references patents, U.S. Pat. Nos. 4,106,488 and 4,303,636 suggests using particles which are of a sufficiently small size, smaller than one micron, so as to be intracellularly absorbed. Gordon then suggested heating these intracellular particles by inductive heating at 50 KHz to 3 MHz to heat the particles and to raise the temperature within the cells wherein the particles are located between 8° C. and 9.5° C. to selectively kill tumor cells and spare normal cells Gordon suggests that tumor cell have a far greater affinity for particles then normal cells and thus should preferentially phagocytose the particles compared to normal cells.

Contary to the suggestions of Gordon outlined above, I have found that magnetic particles of a size smaller than one micron in diameter are preferentially absorbed into certain organs of a body. These include the liver, the spleen, the kidneys, the lungs and other organs which contains reticuloendothelium. Other such organs containing reticuloendothelium would be the blood vessels, the lymph nodes, bone marrow and connective tissue.

Subsequent to the above referred to two patents of Gordons, in a later patent of Gordon, U.S. Pat. No. 4,359,453, Gordon describes the up take of particles of a size of one micron or less into the interior of atherosclerotic plaques and the phagocytizing of such particles by the endothelial and medial smooth muscle cells of the artherosclerotic lesions.

As noted above, in chemotherapy it has been a goal to develop chemotherapeutic agents which are tumor specific. While in theory it might also be a goal to develop particles which are susceptible to uptake only by tumor cells, as noted above contrary to Gordon, I have found that particles which are capable of being heated by hysteresis heating and which are smaller than one micron, can be absorbed by various body organs. In view of this I have found that it is counterindicated to utilize particles for necrosing of neoplasms by hysteresis heating of these particles if the particles are of such a small size so as to allow their uptake into cells. Introducing particles which are of a size enabling them to be taken up by the general cellular population into a body will led to concentration of those particles in certain body organs as I outline above. Even if a concentration of particles are associated with a neoplastic tumor, when the body containing the particles is subjected to hysteresis heating of the particles, the particles which have concentrated in the organs such as the liver, spleen, kidneys, lungs and other tissue containing reticuloendothelium will also be heated rendering unnecessary damage to an already compromise patient.

It is believed that neoplastic cells are susceptible to hyperthermia induced necrosis at a slightly lower temperature than are normal cells. This in fact is the basis of the above noted temperature range of the Gordons patents wherein Gordon describes heating as being done at a temperature above 45.5° C. to kill the tumor cells, i.e. 8° C. above the normal human cell temperature of 37.5° C. and 8.5° C. above tumor cell temperature according to Gordon, but below that temperature wherein the normal cells sustain damage, i.e 46.5° C. Turner, in U.S. Pat. No. 4,341,227, describes similar temperature ranges, i.e. heating above 41.5° C. to cause tumor cell damage and heating above 43° to 45° C. to cause thermal damage to most normal cells.

Because of their invasive nature and their rapid growth, if a very small population of tumor cells remains alive after hyperthermia, possible only just a single tumor cell, the possibility exist for a re-occurrence of the neoplastic disease state in the patient. In view of this, it is necessary to insure, if possible, that there is a "total kill" of all tumor cells. Even though others have suggested selective kill of only the tumor cells by selective absorption of particles by only the tumor cells, it is considered necessary to provide a sufficient particle density to insure total tumor kill even if it requires sacrificing of a peripheral margin of normal cells around the neoplastic cells. It is therefore necessary that a temperature of at least 42° centigrade be achieved in the totality of the tumor environment This cannot be achieved by selective particle uptake of particles by only tumor cells in preference of uptake by normal cells and it further requires obtaining sufficient particle density in the tumor environment which can only be achieved by particles which are of a size greater than that which can be intracellularly absorbed by the cells.

For hysteresis heating of particles, a certain density of the particles is necessary in order to effectively achieve sufficient heat in the vicinity of a neoplastic tumor in order to cause necrosis of the neoplasm. On an industrial scale, induction heating is utilized to achieve very high temperatures for certain metal treatments or the like. The articles being treated in these processes are of an infinitely more massive domain than are the particle sizes which are dispersed into the body of a warm blooded animal. Thus, for instance, an iron bar can be heated to an incandescent temperature because the heat given off by the billions of atoms is additive; whereas finely dispersed particles of the same material can only be heated to a fraction of that temperature.

I have found that particles of a size range of at least one micron are necessary to avoid intracellular uptake and the problems outline above associated with such intracellular uptake. Further particles of a size range of at least two microns are necessary in order to achieve sufficient density to effectively heat the particles and transfer sufficient heat for necrosis of neoplasms with which the particles are associated Because of these factors, an even more preferred size range would be greater than five microns since this insures no intracellular uptake of the particles and further contributes to the particle density to effective heat the tumor environment even at the expense of a few normal cells at the tumor periphery which might be sacrificed in order to achieve an effect tumor "kill".

Insofar as the particles utilized in my process are injected into the bodies of warm blooded animals, they must, in fact, be of a size smaller than the smallest capillary diameter so as to be effectively mobilized within the body of the warm blooded animal. For all practical purposes this size would be at about 50 microns. Thus, a general range of particle sizes utilized for my process would range from 2 to 50 microns with a more preferred range of 5 to 50 microns.

In order to achieve sufficient particle density within the body of the warm blooded animal in proximity to the tumors, particles of the size noted above will be utilized. Particles of the sizes noted above are of a sufficient size so as not to be intracellularly absorbed by either the neoplastic tissue or healthy tissue. If smaller sized particles are utilized such that the particles are capable of being absorbed by these groups of tissue, aside from having the particle accumulate in certain normal healthy organs as noted above followed by damage of these organs during the hysteresis heating of the particles, the individual particles are prevented by the cellular mechanism surrounding the particles from accumulating in a sufficient density in the environment of the neoplastic tissue so as to achieve the preferred heating resulting in the necrosis of the neoplastic tissue. If particles are dispersed, because of intracellular absorption, the desired density of the particle to achieve the preferred heating of the particles cannot be achieved It is generally assumed that particles of only one micron, or smaller, are capable of absorption. In view of this, for my process, particles of at least double this size, and preferably 5 to 50 times the size, are utilized.

Contary to the earlier work of both myself and my co-inventors and others, in order to avoid any neuromuscular response to the alternating magnetic field utilized to heat the particles, the particles should be heated utilizing alternating magnetic fields which are at least 25 KHz. In order to introduce a reasonable margin of error to take into account individual differences in patient response to the alternating magnetic field and other factors, a frequency greater than 30 KHz is preferred.

As noted above, in saline, eddy current heating is detectable at 0.4 KHz and is significant at 100 KHz. To insure a reasonable margin of error for the safety of a warm blooded animal by avoiding the production of significant eddy current heating in that warm blooded animal, in order to take into account any possible individual differences of biological fluids and organs in the warm blooded animal to eddy current heating in response to alternating magnetic fields the frequency wherein there is significant eddy current heating in saline, 100 KHz, is divided by two to arrive at an upper frequency limit of below 50 KHz for the warm blooded animal. This frequency is of course below the detectable onset of dielectric heating at 500 KHz. By utilizing particles of the size range described above, effective hysteresis heating of the particles can be achieved in my presently most preferred working range of from about 30 KHz to 50 KHz without concurrent neuromuscular effects evident at lower frequency ranges, and concurrent dielectric or eddy current heating effects at higher frequency ranges. This presently preferred frequency range can be extended downward to about 25 KHz without encountering severe neuromuscular response.

The particles which undergo hysteresis heating are chosen so as to have a curie point of at least about 42° C. and preferably no greater than 90° C. so as to eliminate any chance of vaporization of water in the body of the warm blooded animal and concurrent release of steam or the like. A more preferred particle range would be particles having a curie point of from about 42° C. to about 65° C. This range insures effective heating of any neoplastic tissue. The higher end of this curie point range insures tumor hyperthermic necrosis even to the expense of a limited amount of normal tissue necrosis around the periphery of the neoplastic tissue in order to insure survival of the warm blooded animal.

Preferably the particles which are utilized for producing the hysteresis heating would be ferromagnetic particles with ferrite particles being my most presently preferred particles. Commercially available ferrite particles can be utilized.

To introduce the particles into the body of the warm blooded animal in proximity of the neoplasm, the particles can be suspended in an appropriate liquid carrier.

Useful as liquid carriers are my pre-polymerized polymeric mixture, as described in my U.S. Pat. No. 4,392,040, saline solution, one of many known medical contrast mediums, and/or human serum. The art skilled, upon this disclosure, will also be appraised of other suitable liquid carriers which could be utilized to introduce the particles into the body of a warm blooded animal.

I claim:

1. A process of effecting necrosis of neoplasms in warm blooded animals as a result of hyperthermia of the neoplasm which comprises:

introducing particles into said warm blooded animal in the proximity of said neoplasm so as to associate said particles with said neoplasm, said particles capable of exhibiting hysteresis heating, said particles of a size of at least two microns in diameter so as to be incapable of being intracellularly absorbed, said particles further having a curie point in the range of 42° C. to 90° C.;

subjecting the area of said warm blooded animal wherein said neoplasm having said particles associated therewith is located to an alternating magnetic field, said field of a frequency greater than 25 KHz and less than 50 KHz wherein said field is capable of causing hysteresis heating of said particles, and is insufficient to cause eddy current and dielectric heating of the surrounding tissue of said warm blooded animal and further said field is of a frequency greater than that capable of causing a neuromuscular response to said field in said warm blooded animal;

maintaining said neoplasm within said field for a time sufficient to heat said particles and said neoplasm, with which said particles are associated, to a temperature of at least 42° C.

2. The process of claim 1 wherein:
   said particles are of a size range of 5 microns to 50 microns.

3. The process of claim 1 wherein:
   said particles are introduced into said warm blooded animal as a suspension of said particles in a liquid carrier.

4. The process of claim 1 wherein:
   said particles are ferromagnetic particles.

5. The process of claim 4 wherein:
   said particles are ferrite particles.

6. The process of claim 5 wherein:
   said particles are introduced into said warm blooded animal as a suspension of said particles in a liquid carrier, and said liquid carrier is chosen from the group consisting of a pre-polymerized polymeric mixture, saline solution, medical contrast medium and human serum.

7. The process of claim 1 wherein:
   said particles have a curie point of from about 42° C. to about 65° C.

8. The process of claim 1 wherein:
   said particles are introduced into said warm blooded animal as a suspension of said particles in a liquid carrier, and said liquid carrier is chosen from the group consisting of a pre-polymerized polymeric mixture, saline solution, medical contrast medium and human serum.

* * * * *